US00PP32631P2

(12) United States Plant Patent
Pieters

(10) Patent No.: US PP32,631 P2
(45) Date of Patent: Dec. 15, 2020

(54) ***CHRYSANTHEMUM* PLANT NAMED 'G21SOU14RE'**

(50) Latin Name: ***Chrysanthemum* X *morifolium***
Varietal Denomination: G21SOU14RE

(71) Applicant: Elien Sofie Pieters, Oostnieuwkerke (BE)

(72) Inventor: Elien Sofie Pieters, Oostnieuwkerke (BE)

(73) Assignee: PARATY B.V.B.A., Oostnieuwkerke (BE)

( * ) Notice: Subject to any disclaimer, the term of this patent is extended or adjusted under 35 U.S.C. 154(b) by 0 days.

(21) Appl. No.: 16/873,463

(22) Filed: Apr. 17, 2020

(51) Int. Cl.
*A01H 5/02* (2018.01)
*A01H 6/14* (2018.01)

(52) U.S. Cl.
USPC ..... Plt./293
CPC ..... *A01H 6/1424* (2018.05)

(58) Field of Classification Search
USPC ..... Plt./293
CPC ..... A01H 6/1424
See application file for complete search history.

*Primary Examiner* — Anne Marie Grunberg
(74) *Attorney, Agent, or Firm* — C. Anne Whealy

(57) ABSTRACT

A new and distinct cultivar of *Chrysanthemum* plant named 'G21SOU14RE', characterized by its upright, outwardly spreading and uniformly rounded plant habit; moderately vigorous growth habit; freely branching habit; dense and full plant habit; flexible stems; dark green-colored leaves; uniform and freely flowering habit; long flowering period; medium-sized decorative-type inflorescences with ray florets that are initially dark red in color becoming lighter red with development; and excellent garden performance.

1 Drawing Sheet

Botanical designation: *Chrysanthemum* X *morifolium*.
Cultivar denomination: 'G21SOU14RE'.

CROSS-REFERENCED TO CLOSELY-RELATED APPLICATIONS

Title: *Chrysanthemum* Plant Named 'G21SOU11OR'.
Applicant: Elien Sofie Pieters
Filed: Concurrently with the instant application having application Ser. No. 16/873,480
Title: *Chrysanthemum* Plant Named 'G21SOU06PI'
Applicant: Elien Sofie Pieters
Filed: Concurrently with the instant application having application Ser. No. 16/873,481
Title: *Chrysanthemum* Plant Named 'G21SOU01WH'
Applicant: Elien Sofie Pieters
Filed: Concurrently with the instant application having application Ser. No. 16/873,464
Title: *Chrysanthemum* Plant Named 'G21SOU04YE'
Applicant: Elien Sofie Pieters
Filed: Concurrently with the instant application having application Ser. No. 16/873,466

STATEMENT REGARDING PRIOR DISCLOSURES BY INVENTOR/APPLICANT

At the filing of this application, no Plant Breeder's Rights applications for the instant plant have been filed by the Applicant/Inventor nor by the Assignee, Paraty B.V.B.A. of Oostnieuwkerke, Belgium.

There have been no offers for sale anywhere in the world prior to the effective filing date of this Application and no accessibility to one of ordinary skill in the art.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* X *morifolium* and hereinafter referred to by the name 'G21SOU14RE'.

The new *Chrysanthemum* plant is a product of a planned breeding program conducted by the Inventor in Oostnieuwkerke, Belgium. The objective of the breeding program is to create new uniformly mounding and freely flowering *Chrysanthemum* plants with unique and attractive inflorescence form and ray floret coloration.

The new *Chrysanthemum* plant is a naturally-occurring whole plant mutation of *Chrysanthemum* X *morifolium* 'Tonato Pink', not patented. The new *Chrysanthemum* plant was discovered and selected by the Inventor as a single flowering plant from within a population of plants of 'Tonato Pink' in a controlled greenhouse environment in Oostnieuwkerke, Belgium in October, 2018.

Asexual reproduction of the new *Chrysanthemum* plant by vegetative terminal cuttings was first conducted in a controlled greenhouse environment in Oostnieuwkerke, Belgium in January, 2019. Asexual reproduction by vegetative terminal cuttings has shown that the unique features of this new *Chrysanthemum* plant are stable and reproduced true to type in successive generations.

SUMMARY OF THE INVENTION

The following traits have been repeatedly observed and are determined to be the unique characteristics of 'G21SOU14RE'. These characteristics in combination distinguish 'G21SOU14RE' as a new and distinct *Chrysanthemum* plant:

1. Upright, outwardly spreading and uniformly rounded plant habit; moderately vigorous growth habit.
2. Freely branching habit; dense and full plant habit; flexible stems.
3. Relatively small dark green-colored leaves.
4. Uniform and freely flowering habit.
5. Long flowering period.
6. Medium-sized decorative-type inflorescences with ray florets that are initially dark red in color becoming lighter red with development.
7. Excellent garden performance.

Plants of the new *Chrysanthemum* can be compared to plants of the mutation parent, 'Tonato Pink'. In side-by-side comparisons, plants of the new *Chrysanthemum* differ primarily from plants of 'Tonato Pink' in ray floret color as ray florets of plants of the new *Chrysanthemum* are initially dark red in color becoming lighter red with development whereas ray florets of plants of 'Tonato Pink' are initially dark pink in color becoming light pink with development.

Plants of the new *Chrysanthemum* can be compared to plants of the *Chrysanthemum* X *morifolium* 'G21SOU11OR', disclosed in a U.S. Plant Patent application filed concurrently having application Ser. No. 16/873,480. In side-by-side comparisons, plants of the new *Chrysanthemum* differ primarily from plants of 'G21SOU11OR' in ray floret color as ray florets of plants of the new *Chrysanthemum* are initially dark red in color becoming lighter red with development whereas ray florets of plants of 'G21SOU11OR' are initially red in color becoming golden orange with development.

Plants of the new *Chrysanthemum* can be compared to plants of the *Chrysanthemum* X *morifolium* 'G21SOU06PI', disclosed in a U.S. Plant Patent application filed concurrently having application Ser. No. 16/873,481. In side-by-side comparisons, plants of the new *Chrysanthemum* differ primarily from plants of 'G21SOU06PI' in ray floret color as ray florets of plants of the new *Chrysanthemum* are initially dark red in color becoming lighter red with development whereas ray florets of plants of 'G21SOU06PI' are initially red in color becoming light purple with development.

Plants of the new *Chrysanthemum* can be compared to plants of the *Chrysanthemum* X *morifolium* 'G21SOU01WH', disclosed in a U.S. Plant Patent application filed concurrently having application Ser. No. 16/873,464. In side-by-side comparisons, plants of the new *Chrysanthemum* differ primarily from plants of 'G21SOU01WH' in ray floret color as ray florets of plants of the new *Chrysanthemum* are initially dark red in color becoming lighter red with development whereas ray florets of plants of 'G21SOU01WH' are initially light pale yellow in color becoming white with development.

Plants of the new *Chrysanthemum* can be compared to plants of the *Chrysanthemum* X *morifolium* 'G21SOU04YE', disclosed in a U.S. Plant Patent application filed concurrently having application Ser. No. 16/873,466. In side-by-side comparisons, plants of the new *Chrysanthemum* differ primarily from plants of 'G21SOU04YE' in ray floret color as ray florets of plants of the new *Chrysanthemum* are initially dark red in color becoming lighter red with development whereas ray florets of plants of 'G21SOU04YE' are bright yellow in color.

Plants of the new *Chrysanthemum* can also be compared to plants of *Chrysanthemum* X *morifolium* 'Jasoda Dark Red', disclosed in U.S. Plant Pat. No. 26,722. In side-by-side comparisons, plants of the new *Chrysanthemum* differ primarily from plants of 'Jasoda Dark Red' in the following characteristics:

1. Plants of the new *Chrysanthemum* are slightly flatter than and not as ball-shaped as plants of 'Jasoda Dark Red'.
2. Leaves of plants of the new *Chrysanthemum* are brighter green in color than leaves of plants of 'Jasoda Dark Red'.
3. Plants of the new *Chrysanthemum* flower about two weeks later than plants of 'Jasoda Dark Red'.
4. Ray florets of plants of the new *Chrysanthemum* are initially red in color becoming lighter red with development whereas ray florets of plants of 'Jasoda Dark Red' are darker red in color.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. The photograph comprises a side perspective view of a typical flowering plant of 'G21SOU14RE' grown in a container.

DETAILED BOTANICAL DESCRIPTION

The aforementioned photograph and following observations and measurements describe plants grown in 19-cm containers in an outdoor nursery in Oostnieuwkerke, Belgium under natural daylengths during the autumn and under cultural practices generally used in commercial *Chrysanthemum* production. During the production of the plants, day temperatures ranged from 20° C. to 25° C. and night temperatures ranged from 12° C. to 18° C. Plants were 20 weeks old when the photograph and detailed description were taken. In the following description, color references are made to The Royal Horticultural Society Colour Chart, 2015 Edition, except where general terms of ordinary dictionary significance are used.

Botanical classification: *Chrysanthemum* X *morifolium* 'G21SOU14RE'.

Parentage: Naturally-occurring whole plant mutation of *Chrysanthemum* X *morifolium* 'Tonato Pink', not patented.

Propagation:

*Type cutting*.—By vegetative tip cuttings.

*Time to initiate roots, summer*.—About two weeks at temperatures about 20° C.

*Time to initiate roots, winter*.—About 20 days at temperatures about 20° C.

*Time to produce a rooted young plant, summer*.—About 30 days at temperatures about 20° C.

*Time to produce a rooted young plant, winter*.—About 40 days at temperatures about 20° C.

*Root description*.—Fine, fibrous; typically light brown in color, actual color of the roots is dependent on substrate composition, water quality, fertilizer type and formulation, substrate temperature and physiological age of roots.

*Rooting habit*.—Freely branching; medium density.

Plant description:

*Appearance*.—Perennial decorative-type *Chrysanthemum* with oblong ray florets; stems upright and outwardly spreading giving a uniformly rounded appearance to the plant; plants roughly spherical; very freely branching habit, about 25 to 30 primary lateral branches develop, each primary lateral branch with multiple secondary branches; pinching enhances lateral branch development; dense and full plant habit; moderately vigorous growth habit; moderate growth rate; plants flexible, not brittle.

*Plant height*.—About 40 cm.

*Plant width*.—About 50 cm.

*Lateral branches*.—Length: About 25 cm. Diameter: About 2 mm to 3 mm. Internode length: About 2 cm. Strength: Moderately strong, flexible. Texture: Pubescent, fine; longitudinally ridged. Color: Close to 137A.

*Leaves*.—Arrangement: Alternate, simple. Length: About 3 cm to 5 cm. Width: About 2.5 cm to 3 cm. Apex: Rounded to cuspidate. Base: Attenuate. Margin: Palmately lobed and serrate, sinuses between lateral lobes divergent to parallel. Texture, upper and lower surfaces: Slightly pubescent. Venation: Palmately reticulate. Color: Developing leaves, upper surface: Close to 137C. Developing leaves, lower surface: Close to 137D. Fully expanded leaves, upper surface: Close to N137C; venation, close to 148C. Fully expanded leaves, lower surface: Close to 147B; venation, close to 147B to 147C. Petioles: Length: About 1 cm. Diameter: About 2 mm. Texture, upper and lower surfaces: Slightly pubescent; slightly rough. Color, upper surface: Close to 146C. Color, lower surface: Close to 146D. Stipules: Length: About 1 cm. Diameter: About 2 mm. Texture, upper and lower surfaces: Slightly pubescent. Color, upper and lower surfaces: Close to 137A.

Inflorescence description:

*Appearance*.—Decorative-type inflorescence form; inflorescences borne on terminals above foliar plane; disc and ray florets arranged acropetally on a capitulum.

*Fragrance*.—Slightly fragrant, pungent.

*Flowering response*.—Under natural season conditions, plants flower in mid-October in Belgium; flowering response time, about 40 days.

*Postproduction longevity*.—Inflorescences maintain good color and substance for about 42 days; inflorescences persistent.

*Quantity of inflorescences*.—About 30 to 35 inflorescences develop per lateral branch.

*Inflorescence buds*.—Height: About 9 mm. Diameter: About 1.4 cm. Shape: Globular. Color: Close to 183A.

*Inflorescence diameter*.—About 4 cm.

*Inflorescence depth* (*height*).—About 3.5 cm.

*Disc diameter*.—About 3 mm; inconspicuous.

*Receptacle diameter*.—About 3 mm.

*Receptacle height*.—About 2.5 mm to 3 mm.

*Receptacle color*.—Close to 144B.

*Ray florets*.—Number of ray florets per inflorescence: About 150 to 200 arranged in about ten whorls. Length: About 3.5 cm to 5 cm. Width: About 7 mm. Shape: Oblong. Apex: Rounded. Base: Attenuate. Margin: Entire. Aspect: Mostly horizontal. Texture and luster, upper and lower surfaces: Smooth, glabrous; matte. Color: When opening, upper surface: Close to 183A. When opening, lower surface: Close to 179A. Fully opened, upper surface: Close to 179A; venation, close to 179A; color becoming closer to 178B with development. Fully opened, lower surface: Close to 180C; venation, close to 180C; color becoming closer to 180D with development.

*Disc florets*.—Number of disc florets per inflorescence: About 20 massed at the center of the inflorescence. Length: About 3 mm. Diameter: About 0.5 mm to 1 mm. Shape: Tubular; apices dentate. Texture and luster: Smooth, glabrous; glossy. Color, immature: Close to 145A. Color, mature: Close to 12A.

*Phyllaries*.—Number of phyllaries per inflorescence: About 25 arranged in two or three whorls. Length: About 4 mm to 6 mm. Width: About 2 mm to 3 mm. Shape: Ovate. Apex: Rounded. Base: Rounded to truncate. Margin: Entire. Texture, upper and lower surfaces: Smooth, glabrous. Color, upper surface: Close to 137A. Color, lower surface: Close to N137B.

*Peduncles*.—Length, terminal peduncle: About 5 cm. Length, fourth peduncle: About 5 cm. Length, seventh peduncle: About 5 cm. Diameter: About 2 mm. Angle: About 30° from vertical. Strength: Moderately strong. Texture: Slightly pubescent. Color: Close to 137C.

*Reproductive organs*.—Androecium: Stamen development has not been observed on inflorescences of the new *Chrysanthemum*. Gynoecium: Pistil development has not been observed on inflorescences of the new *Chrysanthemum*.

*Seeds and fruits*.—To date seed and fruit production have not been observed on plants of the new *Chrysanthemum*.

Garden performance: Plants of the new *Chrysanthemum* have demonstrated excellent garden performance and will tolerate temperatures ranging from about 1° C. to about 45° C.

It is claimed:

1. A new and distinct *Chrysanthemum* plant named 'G21SOU14RE' as illustrated and described.

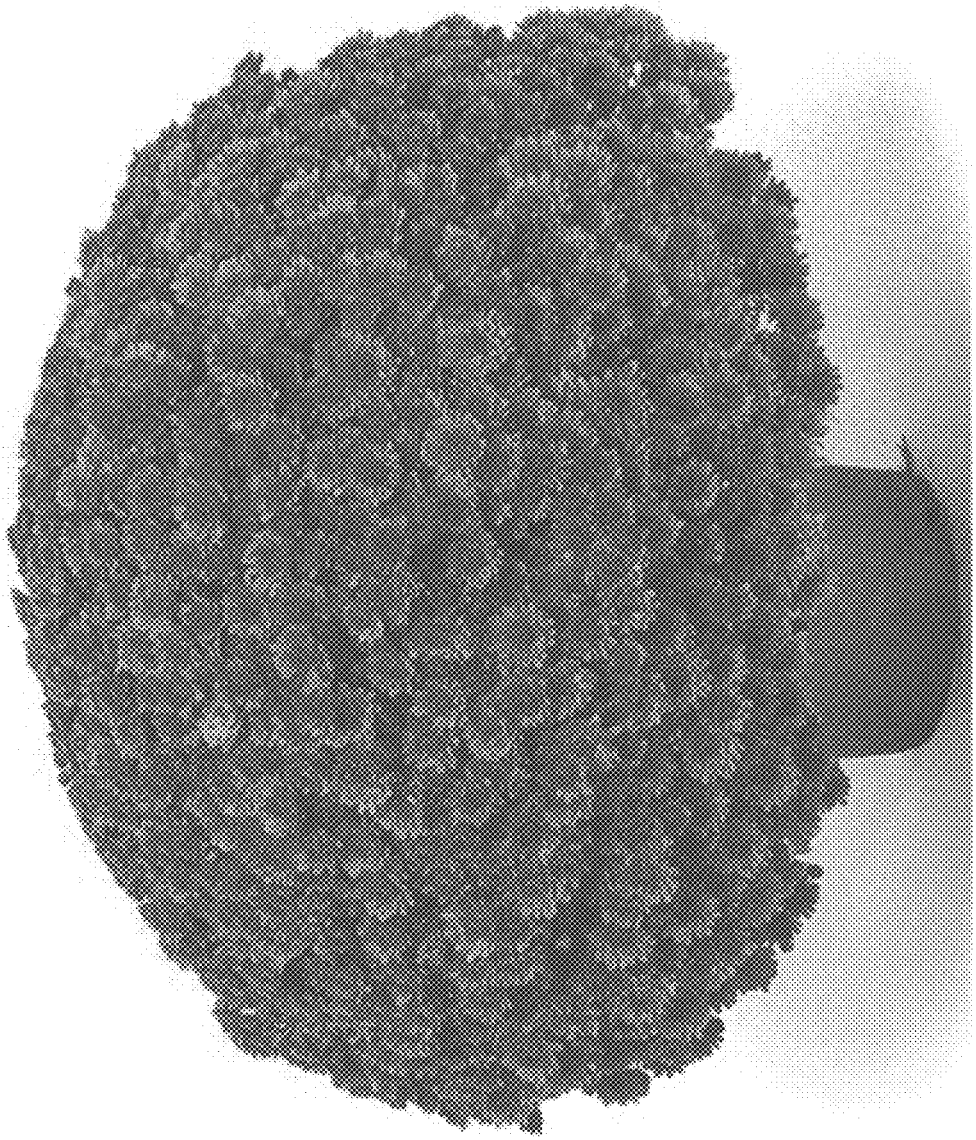

* * * * *